United States Patent [19]

Arndt et al.

[11] Patent Number: 4,487,725
[45] Date of Patent: Dec. 11, 1984

[54] PROCESS FOR THE PREPARATION OF N-ACETYLAMINOARYLSULFONIC ACIDS IN SULFURIC ACID AS SOLVENT

[75] Inventors: Otto Arndt, Hofheim am Taunus; Theodor Papenfuhs, Frankfurt am Main, both of Fed. Rep. of Germany

[73] Assignee: Hoechst Aktiengesellschaft, Fed. Rep. of Germany

[21] Appl. No.: 495,510

[22] Filed: May 17, 1983

[30] Foreign Application Priority Data

May 26, 1982 [DE] Fed. Rep. of Germany ....... 3219651

[51] Int. Cl.³ .................. C07C 143/58; C07C 143/60
[52] U.S. Cl. ............................ 260/507 R; 260/543 R
[58] Field of Search .................................. 260/507 R

[56] References Cited

PUBLICATIONS

Donaldson, "The Chemistry and Technology of Naphthalene Compound", Edward Arnold (Publishers) Ltd., London, 1958, p. 334.
Sandler et al., "Organic Functional Preparations", Academic Press, New York, vol. I, 1968, pp. 274–282.

Primary Examiner—Nicky Chan
Attorney, Agent, or Firm—Connolly and Hutz

[57] ABSTRACT

The invention relates to salt-free N-acetylaminoarylsulfonic acids, their preparation by acetylation with acetic anhydride or acetyl chloride, sulfuric acid, which can also contain a small amount of water and/or dimethylformamide and/or N-methylpyrrolidone, serving as the solvent, and the use of the N-acetylaminoarylsulfonic acids for the preparation of their acid chlorides.

5 Claims, No Drawings

PROCESS FOR THE PREPARATION OF N-ACETYLAMINOARYLSULFONIC ACIDS IN SULFURIC ACID AS SOLVENT

The invention relates to salt-free N-acetylaminoarylsulfonic acids, a process for their preparation and their use for the preparation of the N-acetylaminoarylsulfonyl chlorides.

Salts of N-acetylaminosulfonic acids, in particular those derived from benzene and naphthalene, have been known for many years, as have some of the corresponding free acids, for example N-acetylsulfanilic acid (p-acetaminobenzenesulfonic acid, p-acetanilinesulfonic acid) and N-acetyl-naphthionic acid (4-acetaminonaphthalene-1-sulfonic acid).

In order to prepare these N-acetylaminoarylsulfonic acids, it is possible to distinguish in principle between the introduction of sulfonic acid groups into N-acetylaminoarenes on the one hand and acetylation on the amino group of aminoarylsulfonic acids on the other.

The following may be mentioned from the former group of preparation processes: introduction of acetanilide into fuming sulfuric acid and heating the solution obtained for several hours; isolation of N-acetylaminobenzenesulfonic acid was not possible (Ber. 18 (1885) 296). In contrast, using fuming sulfuric acid, it was possible to obtain p-acetanilinesulfonic acid and N-acetylated sulfonic acids of p-toluidine and of 1,4,2- and 1,3,4-xylidine in crystalline form (Ber. 33 (1900) 1364/6). N-Acetylsulfanilic acid has also been obtained from acetanilide using "acetylsulfuric acid" (from concentrated sulfuric acid and acetic anhydride) (Ber. 42 (1909) 4539). It was established, on the basis of kinetic studies, that, at concentrations >70% of sulfuric acids which contain water, the sulfonation predominates over hydrolysis of the N-acetyl group (Chem. & Ind. 36 (1970) 1172, Tetrahedron Letters 1971, 2161/2). Finally, in order to introduce sulfonic acid groups, products of nuclear halogen substitution of acetanilide have been reacted with acid or neutral sulfites with the formation of N-acetylaminobenzenesulfonic acids or their salts (German Pat. No. 101,777, Friedl. 5 754/6).

None of these processes are suitable for the preparation of N-acetylaminoarylsulfonic acids on an industrial scale.

The following may be mentioned from the second group of preparation processes mentioned above:

Reaction of, for example, sodium sulfanilate in aqueous solution with ketene (German Pat. No. 453,577, Friedl. 16 237/9). Because of the toxicity and difficulty in manipulating ketene, this process is not very suitable for being carried out on an industrial scale.

Reaction of dry powdered Na, K or Ba salts of aminosulfonic acids of benzene and naphthalene with acetic anhydride (Ber. 17 (1884) 707/8, 21 (1888) 2579/82, 39 (1906) 1559/70, 58 (1925) 2287, J. Prakt. Chem. (2) 63 (1902) 406/9), or of the Na salt with glacial acetic acid (German Pat. No. 92,796, Friedl. 4 1152).

Reaction of salts of the aminosulfonic acids of the benzene and naphthalene series, in aqueous solution or suspension, with acetic anhydride (German Pat. No. 129,000, Friedl. 6 215/7, Ber. 46 (1913) 777, Bull. Soc. Chim. France (5) 21 (1954) 97/8) or with acetic acid and acetic anhydride (German Pat. No. 410,364, Friedl. 15 133, Ber. 33 (1900) 417, J. Org. Chem. 6, 25 (1941).

Reaction of aminosulfonic acids of benzene and naphthalene in pyridine with acetic anhydride, optionally with addition of glacial acetic acid (J. Soc. Chem. Ind. 46 (1927) 224 T / 226 T, 47 (1928) 155 T - 157 T, J. Soc. Dyers Colourists 59 (1943) 144/8, Synthesis 12, 1974 877/8).

While the acetylation in the abovementioned processes leads, in a highly exothermic reaction, to the salts (metal or pyridinium salts) of the N-acetylaminoarylsulfonic acids, acetylation of the free aminoarylsulfonic acids only succeeds in exceptional cases, for example with o-toluidinesulfonic acid (Ber. 17 (1884) 707/8). o-, m- and p-Aminobenzenesulfonic acids do not react even on heating with acetic anhydride at 100° to 140°0 C. for 10 hours (Bull. Soc. Chim. France (5) 21 (1954) 98).

The preferred industrial process for the preparation of the Na salt of N-acetylsulfanilic acid has hitherto been the reaction of sodium sulfanilate (from sulfanilic acid and sodium carbonate) in aqueous solution with acetic anhydride (Ullmanns Encyclopadie der Technischen Chemie (Ullmann's Encyclopedia of Industrial Chemistry), 4th edition, Vol. 8, p. 426 following IOS Final Rept. No. 1149, p. 125/6).

The free N-acetylaminoarylsulfonic acids are obtained from the aqueous solutions of their salts by treatment with strong mineral acids (German application J 4736, Friedl. 5 756, Ber. 39 (1906) 1559/70). This produces acids which contain considerable amounts of salts of mineral acids which do not in fact make it impossible to regenerate the acids, but do greatly increase the costs associated with this.

For reasons of cost and for ecological reasons, there is a pressing need for a process in which aminoarylsulfonic acids in the free form can be acetylated.

It has now been found that aminoarylsulfonic acids can be acetylated with acetic anhydride or acetyl chloride in sulfuric acid as the solvent to give N-acetylaminoarylsulfonic acids.

A process has been found for the preparation of N-acetylaminoarylsulfonic acids by acetylation of aminoarylsulfonic acids with acetic anhydride or acetyl chloride which comprises undertaking the acetylation in sulfuric acid as the solvent.

In the case of acetic anhydride, acetic acid is formed and remains in the reaction mixture, and in the case of acetyl chloride, gaseous HCl escapes.

The sulfuric acid should preferably contain a small amount of water and/or dimethylformamide and/or N-methylpyrrolidone. Advantageously, up to 2% by weight, in particular up to 1% by weight, of water or up to 3% by weight, in particular up to 2.5% by weight, of dimethylformamide or N-methylpyrrolidone is employed, in each case relative to the sulfuric acid.

In the case where only sulfuric acid is initially introduced, the sulfuric acid js advantageously employed in a minimum amount of about 4 to 5 moles per mole of aminoarylsulfonic acid in order to maintain good stirrability of the reaction mixture. If the acetylating agent, namely acetic anhydride or acetyl chloride, is initially introduced together with the sulfuric acid, then the minimum amount of sulfuric acid decreases to about 2 to 3 moles per mole of aminoarylsulfonic acid.

The acetylating agent is advantageously employed in an amount of about 1.25 to about 2 moles per mole of aminoarylsulfonic acid.

Advantageously, either sulfuric acid or sulfuric acid plus acetylating agent are initially introduced and, at room temperature (about 25° C.), either the anhydrous and salt-free powdered aminoarylsulfonic acid and the acetylating agent or only the aminoarylsulfonic acid respectively are introduced. It is occasionally necessary also to increase the temperature somewhat during this introduction in order to improve the stirrability of the reaction mixture. After introduction is complete, the temperature is then raised to about 60° to about 90° C., depending on the aminoarylsulfonic acid to be acetylated.

The progress of the acetylation is advantageously followed using thin-layer chromatography of the unacetylated aminosulfonic acid still remaining. If necessary, further acetylating agent required can be added through the charging valve.

In general, readily stirrable, moderately viscous solutions or suspensions of the N-acetylaminoarylsulfonic acids are obtained, which can either be used directly for the reaction to give the corresponding sulfonyl chloride or discharged while still hot into initially introduced water, with stirring, to isolate the N-acetylaminoarylsulfonic acids.

During this, the hydrates of the N-acetylaminoarylsulfonic acids crystallize out. In order to obtain ready filterability it is advantageous to maintain a temperature of about 30° to about 40° C. The amount of initially introduced water is advantageously adjusted such that filtrate acids containing at least about 30% of sulfuric acid and at least about 20% of acetic acid are obtained.

The N-acetylaminoarylsulfonic acids which have been filtered off are advantageously washed with about 3 to about 6 moles of HCl, in the form of about 20–30% strength hydrochloric acid, until free of sulfuric acid. The filtered material is advantageously stirred into a portion of the hydrochloric acid, filtered again and washed with the remainder of the hydrochloric acid. However, the product can also be left on the filter and the entire amount of hydrochloric acid used for washing.

A hydrochloric acid which contains a few per cent of sulfuric acid and also acetic acid is obtained on washing. Due to the ready solubility of the N-acetylaminoarylsulfonic acids in water, a final washing with water would be associated with more or less substantial losses of the substance. However, the washing with hydrochloric acid described considerably reduces the losses. The N-acetylaminoarylsulfonic acids are obtained as moist products which are free of sulfuric acid and contain hydrochloric acid and which can be freed of HCl and water, advantageously in a corrosion-resistant dryer, for example in an enameled double-cone dryer, at temperatures up to 120° C., preferably under reduced pressure. The dried products contain, at the most, traces of aminoarylsulfonic acid and small amounts of water. The products thus dried are optionally also milled. They can then be easily metered.

The yields are 90 to 95% of theory.

The moist products can also be dehydrated by heating with organic materials, for example high-boiling petroleum fractions (in particular with boiling points from 110° to 140° C.) and distilling out these azeotroping agents in an enameled stirred vessel.

The sulfuric acid must be washed out as nearly quantitatively as possible, so that no sulfonation of the N-acetylaminoarylsulfonic acids obtained takes place at the high drying temperatures.

The filtrate acids (sulfuric acid containing acetic acid and hydrochloric acid containing small amounts of sulfuric acid and acetic acid) are freed of volatile constituents (HCl and acetic acid) and concentrated in a known manner. This regeneration is no problem, since no interfering salts are present. Moreover, it leaves behind no residues which would have to be discharged to the sewers.

Using the process according to the invention, aminoarylsulfonic acids, preferably those of benzene and naphthalene, which can also be substituted on the nucleus, preferably alkyl-substituted, particularly preferably methylated, in particular the o-, m- and p-aminobenzenesulfonic acids and the 1,4-, 2,6- and 2,8-aminonaphthalenesulfonic acids can be acetylated to give their N-acetyl derivatives.

The N-acetylaminoarylsulfonic acids obtained can, as already mentioned above, either be used in the form of the solution or suspension obtained after the acetylation reaction or as the isolated and dried substances for the preparation of the corresponding sulfonyl chlorides.

According to the state of the art, the following processes have been described for the preparation of N-acetylaminoarylsulfonyl chlorides:

From acetanilide and chlorosulfonic acid or oleum and chlorosulfonic acid, in addition other chlorinating agents of the acid chloride type, for example phosphorus trichloride and phosphorus pentachloride and, preferably, thionyl chloride, also being used (German Pat. No. 752,572, Ber. 39 (1906) 1559/70, 46 (1913) 777, Zh. Prikl. Khim. 11 (1938) 316/27, C. Z. 1939 I 4934/6).

Reaction of metal salts (Zh. Prikl. Khim. 34 (1961) 625/7, J. Appl. Chem. U.S.S.R. (English translation) 34 (1961) 1549/51, German Pat. No. 532,399, Friedl. 18 601/4, GDR Pat. 30,312, Organic Syntheses Collective Vol. I, p. 8/10, New York-London, 2nd ed.) or of pyridinium salts (Synthesis 1974 p. 877/8) of N-acetylaminoarylsulfonic acids with chlorosulfonic acid or with phosphorus pentachloride (Ann. 380 (1911) 309).

While sulfochlorination of aromatic acetamino compounds only leads to a few representatives of acetaminoarylsulfonyl chlorides, and these moreover in unsatisfactory yields, the preparation via the salts of the N-acetylaminoarylsulfonic acids is associated with the same disadvantages as described above for the preparation of the free N-acetylaminoarylsulfonic acids: Production of considerable amounts of filtrate acids, the regeneration of which is greatly interfered with by the metal ions contained therein.

The use of the salt-free N-acetylaminoarylsulfonic acids obtained according to the invention provides the possibility of salt-free preparation of their chlorides.

When using the solution or suspension obtained after the acetylation reaction, an excess of thionyl chloride, as the preferred chlorinating agent, is necessary, and this depends on the amount of sulfuric acid dissolved in the N-acetylaminoarylsulfonic acid. The sulfuric acid reacts with the thionyl chloride with the formation of chlorosulfonic acid. At the same time, the N-acetylaminoarylsulfonic acid is chlorinated to give the acid chloride. Chlorosulfonic acid can optionally be added to the solution of the N-acetylaminoarylsulfonic acid in sulfuric acid before the addition of thionyl chloride.

If the isolated and dried N-acetylaminoarylsulfonic acid is used, this is advantageously dissolved in chlorosulfonic acid and chlorinated with thionyl chloride to give the acid chloride.

In both cases of this preferred use of thionyl chloride as the chlorinating agent, $SO_2$ and HCl are produced as waste gases which can be separated out without problems in a known manner in devices for washing gases.

In both cases, the reaction with thionyl chloride is advantageously carried out at 30° to 70° C., preferably 50° to 60° C. After completion of addition of the thionyl chloride, the mixture is further stirred at the same temperature for some time.

The reaction with thionyl chloride is promoted by the addition of small amounts of dimethylformamide (Helv. Chim. Acta 42 (1959) 1653–1658).

After evolution of gas has ceased, the reaction mixture obtained is discharged into ice-water. During this, the N-acetylaminoarylsulfonyl chloride precipitates out. The precipitated product is filtered off with suction, washed with ice-water and either used further in the moist form or, advantageously, dried in a drying oven in a thin layer under reduced pressure and at a temperature up to about 50° C., while passing through a stream of dry nitrogen.

As when N-acetylaminoarylsulfonic acids are prepared according to the invention, preparation of their acid chlorides produces filtrate and washing liquors which can be regenerated or worked up without problems, since they do not contain any salts which interfere with these processes.

Naturally, the metal salts of the aminoarylsulfonic acids can also be acetylated by the process according to the invention, but then, as stated above, the N-acetylaminoarylsulfonic acids are not obtained free of salts, and filtrate and washing liquors are produced, the possibility of regeneration of which is considerably restricted by the salts contained therein.

The N-acetylaminoarylsulfonic acids and their chlorides are valuable intermediate products in the preparation of derivatives of aminoarylsulfonic acids (for example, their acid chlorides and amides or sulfones). This is because it is frequently necessary, before carrying out the particular reaction, to protect the amino group by introducing an acetyl group. The acetyl group is split off again by hydrolysis in a suitable subsequent stage of the process.

EXAMPLES

In the following examples, parts always denote parts by weight unless otherwise specified. Likewise, reported percentages relate to the weight unless otherwise specified.

EXAMPLE 1

(a) m-Acetaminobenzenesulfonic acid (N-acetylmetanilic acid).

866 parts of dried metanilic acid were introduced with stirring over 1 hour at a temperature gradually rising from about 20° to about 40° C. into a mixture, prepared at about 20° C., of 645 parts of acetic anhydride and 1,005 parts of 99.5% strength sulfuric acid in a three-necked glass flask provided with a stirrer. To complete the acetylation, the mixture was heated to about 80° C. and stirred further at this temperature while a further 60 parts of acetic anhydride where metered in. The reaction mixture was then stirred into 1,000 parts of water at about 35° C. initially introduced into an open vessel, whereupon N-acetylmetanilic acid crystallized out in the form of a hydrate. It was stirred further at approximately 15° C. and filtered off with suction. 1,350 parts of an approximately 75% pure product (containing adherent aqueous sulfuric and acetic acids) was obtained and stirred into 1,355 parts of 26% strength hydrochloric acid at about 5° C. initially introduced into an open glass vessel. The white suspension produced was filtered off with suction and washed with 580 parts of 31% strength hydrochloric acid.

1,380 parts of an approximately 73% pure N-acetylmetanilic acid hydrate which was free of sulfuric acid and contained about 100 parts of hydrogen chloride were obtained. The product was dried in a drying oven in a stream of nitrogen under about 200 mbar at a temperature slowly rising from about 25° to 120° C., and then milled.

1,020 parts of N-acetylmetanilic acid were obtained as an approximately 99% pure powder having a melting point of 215°–220° C., which corresponded to a yield of 95% of theory.

In addition, the following were obtained:

2,180 parts of an approximately 40% strength filtrate sulfuric acid which was free of salt and hydrochloric acid and could be regenerated and contained 430 parts of acetic acid, 1,820 parts of an approximately 22% strength filtrate hydrochloric acid containing 100 parts of sulfuric acid and 35 parts of acetic acid.

(b) N-Acetylmetanilyl chloride.

233 parts of chlorosulfonic acid were initially introduced into a glass flask provided with a gas-tight stirrer and connectors for introducing and discharging gas, and 215 parts of the N-acetylmetanilic acid obtained according to Example 1 a were introduced using a screw metering device, with stirring, over 1 hour at a temperature slowly rising from about 25° to about 55° C. Then 238 parts of thionyl chloride were allowed to run in over 4 hours at about 55° C. After evolution of gas had ceased (HCl and SO$_2$; absorbing the former in a customary manner by initially passing through water and the latter then in sodium hydroxide solution), the reaction mixture was stirred into 1,000 parts of ice-water (from 800 parts of water and 200 parts of ice) in which 30 parts of powdered active charcoal had been suspended. The precipitated product was filtered off with suction and washed with 800 parts of ice-water. The wash filtrate served to precipitate the next batch.

210 parts of N-acetylmetanilyl chloride were obtained as a technical moist product in a yield of 83% of theory relative to metanilic acid.

In addition, the following were obtained: 1,130 parts of approximately 15% strength sulfuric acid which was free of salt and could be regenerated and contained 65 parts of hydrogen chloride and 17 parts of metanilic acid, 800 parts of wash filtrate containing 10 parts of hydrogen chloride and 15 parts of sulfuric acid, 300 parts of approximately 23% strength hydrochloric acid (from the waste gas washing) containing about 20 parts of SO$_2$, 200 parts of an approximately 25% strength sodium bisulfite solution which was almost free of chloride (from the waste gas washing).

EXAMPLES 2 to 9

N-Acetylmetanilyl chloride without intermediate isolation of N-acetylmetanilic acid.

EXAMPLE 2

159 parts of acetyl chloride were initially introduced into the glass flask used in Example 1b and 200 parts of anhydrous sulfuric acid were added dropwise at 20° C., with stirring and external cooling. Then 173 parts of dry metanilic acid were introduced using a screw metering device at about 45° C. In order to complete the acetylation, the mixture was heated to about 95° C.

After cooling down, the solution of N-acetylmetanilic acid obtained was diluted, without intermediate isolation, at about 30° C. with 233 parts of chlorosulfonic acid. 417 parts of thionyl chloride were allowed to run in, with stirring, over about 4 hours at about 55° C. After evolution of gas had ceased ($SO_2$ and HCl; these being absorbed in the customary manner described in Example 1b), the reaction mixture was stirred into 1,500 parts of ice-water (750 parts each of water and ice) in which 30 parts of powdered active charcoal had been suspended. The precipitated product was filtered off with suction and washed with 1,500 parts of ice-water. The wash filtrate can serve to precipitate the next batch.

210 parts of N-acetylmetanilyl chloride were obtained as a technical moist product in a yield of 90% of theory relative to metanilic acid.

In addition, the following were obtained: 1,763 parts of approximately 19% strength filtrate sulfuric acid which was free of salt and could be regenerated and contained 127 parts of hydrogen chloride, 30 parts of acetic acid and 17 parts of metanilic acid, 1,546 parts of wash filtrate coqtaining 15 parts of hydrogen chloride and 40 parts of sulfuric acid, 771 parts of approximately 27% strength hydrochloric acid (from the waste gas washing) containing 60 parts of $SO_2$ and 30 parts of acetic acid, 1,008 parts of an approximately 21% strength sodium bisulfite solution (from the waste gas washing) which was almost free of chloride.

EXAMPLE 3

865 parts of dry metanilic acid were introduced over 1 hour using a screw metering device, with stirring, into a mixture, prepared at about 20° C., of 645 parts of acetic anhydride and 1,000 parts of anhydrous sulfuric acid in the glass flask used in Example 1b at a temperature rising gradually from about 20° to about 40° C. In order to complete the acetylation, the mixture was heated to about 85° C. and further stirred at this temperature while a further 60 parts of acetic anhydride were metered in.

After cooling down to about 50° C., the solution of N-acetylmetanilic acid obtained was diluted, without intermediate isolation, with 583 parts of chlorosulfonic acid. 2,678 parts of thionyl chloride were allowed to run in, with stirring, over about 8 hours at about 55° C. The mixture was then further stirred for 2 hours at about 55° C. After evolution of gas had ceased ($SO_2$ and HCl; their absorption taking place in the customary manner described in Example 1b), the reaction mixture was freed of residual gases in a stream of dry nitrogen and then stirred into 5,500 parts of ice-water (2,750 parts each of water and ice). The precipitated product was filtered off with suction and washed with 5,500 parts of ice-water. The wash filtrate served to precipitate the next batch.

935 parts of N-acetylmetanilyl chloride obtained as a technical moist product in a yield of 80% of theory relative to metanilic acid.

The rubber-like, sticky state of the product occurring at the start of the precipitation could be prevented by suspending 150 parts of powdered active charcoal or 100 parts of product from an earlier batch in the 5,500 parts of ice-water before the precipitation.

In addition, the following were obtained: 6,700 parts of approximately 19% strength filtrate sulfuric acid which was free of salt and could be regenerated and contained 430 parts of hydrogen chloride, 430 parts of acetic acid and 170 parts of metanilic acid, 5,000 parts of wash filtrate containing 80 parts of hydrogen chloride and 210 parts of sulfuric acid, 4,700 parts of approximately 25% strength hydrochloric acid (from the waste gas washing) containing 205 parts of $SO_2$ and 140 parts of acetic acid, 8,200 parts of an approximately 22% strength sodium bisulfite solution (from the waste gas washing) which was almost free of chloride (sodium chloride content<1%) having a small content (<10 parts) of acetic acid.

EXAMPLE 4

The procedure was as in Example 3 with the difference that 2,975 parts of thionyl chloride were allowed to run in over 10 hours.

Again, 935 parts of N-acetylmetanilyl chloride were obtained, which corresponded to an unchanged yield of 80% of theory.

EXAMPLE 5

The procedure was as in Example 3 with the difference that 25 parts of dimethylformamide were allowed to run into the reaction mixture immediately before the addition of the thionyl chloride.

970 parts of N-acetylmetanilyl chloride were obtained, which corresponded to a yield of 83% of theory. 240 parts of acetic acid were found in the hydrogen chloride from the waste gas washing.

EXAMPLE 6

The procedure was as in Example 4 with the difference that 25 parts of dimethylformamide were added to the mixture of 645 parts of acetic anhydride and 1,000 parts of anhydrous sulfuric acid.

1,040 parts of N-acetylmetanilyl chloride were obtained, which corresponded to a yield of 89% of theory.

EXAMPLE 7

The procedure was as in Example 4 with the difference that 5 parts of water were added to the 1,000 parts of anhydrous sulfuric acid.

1,017 parts of N-acetylmetanilyl chloride were obtained, which corresponded to a yield of 87% of theory.

EXAMPLE 8

The procedure was as in Example 7 with the difference that 10 parts of water were added.

Again, 1,017 parts of N-acetylmetanilyl chloride were obtained.

Example 9

The procedure was as in both Example 7 and Example 5. 1,040 parts of N-acetylmetanilyl chloride were obtained, which corresponded to a yield of 89% of theory.

EXAMPLE 10

(a) p-Acetaminobenzenesulfonic acid (N-acetylsulfanilic acid).

A mixture, prepared at about 15° C., of 205 parts of acetic anhydride, 5 parts of dimethylformamide and 300 parts of anhydrous sulfuric acid was initially introduced into the glass flask used in Example 1a. 173 parts of dried sulfanilic acid were introduced while stirring over 1 hour at a temperature gradually rising from about 15° to about 30° C. In order to complete the acetylation, the mixture was heated to about 65° C. and stirred further at this temperature. The reaction mixture was then stirred into 300 parts of water at about 35° C., whereupon N-acetylsulfanilic acid crystallized out in the form of a hydrate. The crystallization was completed by further stirring at about 15° C. After filtration with suction, 293 parts of an approximately 60% pure product were obtained which were stirred into 500 parts of 26% strength hydrochloric acid at about 5° C. The white suspension produced was filtered off with suction and washed with 250 parts of cold 26% strength hydrochloric acid.

304 parts of an N-acetylsulfanilic acid hydrate which was free of sulfuric acid and contained hydrochloric acid were obtained. The product was dried in a drying oven in a stream of nitrogen under about 200 mbar at a temperature which slowly rose from about 25° to about 90° C.

193 parts of N-acetylsulfanilic acid were obtained as a 99% pure powder having a melting point of 243°–246° C., which corresponded to a yield of 90% of theory.

In addition, the following were obtained:

733 parts of an approximately 35% strength filtrate sulfuric acid which was free of salt and hydrochloric acid and could be regenerated and contained 144 parts of acetic acid, 712 parts of an approximately 21% strength filtrate hydrochloric acid containing 25 parts of sulfuric acid and 10 parts of acetic acid.

(b) p-Acetaminobenzenesulfonyl chloride (N-acetylsulfanilyl chloride)

117 parts of chlorosulfonic acid were initially introduced into the glass flask used in Example 1b and, with stirring, 114 parts of the N-acetylsulfanilic acid obtained according to Example 10 a were introduced over 1 hour at a temperature slowly rising from about 25 to about 45° C. After solution was complete, 2.50 parts of dimethylformamide were added. 119 parts of thionyl chloride were then allowed to run in over 4 hours at about 50°–55° C. The mixture was stirred for a further 2 hours at 50°–55° C. After evolution of gas had ceased (HCl and SO$_2$; their absorption took place in the customary manner described in Example 1b), the reaction mixture was freed of residual gases in a stream of dry nitrogen and then stirred into 500 parts of ice-water (250 parts each of water and ice). The precipitated product was filtered off with suction and washed with 500 parts of ice-water. 119 parts of p-acetaminobenzenesulfonyl chloride were obtained as a technical moist product in a yield of 86% of theory relative to sulfanilic acid.

In addition, the following were obtained:

640 parts of approximately 22% strength sulfuric acid which was free of salt and could be regenerated and contained 43 parts of hydrogen chloride, 480 parts of wash filtrate containing 6 parts of hydrogen chloride and 13 parts of sulfuric acid, 140 parts of approximately 20% strength hydrochloric acid (from the waste gas washing) containing 13 parts of SO$_2$, 95 parts of approximately 20% strength sodium bisulfite solution (from the waste gas washing).

EXAMPLE 11 o-Acetaminobenzenesulfonic acid (N-acetylorthanilic acid)

The procedure was as in Example 10 a with the difference that, in place of 173 parts of sulfanilic acid, the same amount of dried orthanilic acid was employed.

133 parts of N-acetylorthanilic acid were obtained as an approximately 97% pure powder of melting point 228°–230° C. The yield was 62% of theory.

In addition, the following were obtained:

723 parts of an approximately 36% strength filtrate sulfuric acid which was free of salt and hydrochloric acid and could be regenerated and contained 155 parts of acetic acid, 793 parts of an approximately 22% strength filtrate hydrochloric acid containing 36 parts of sulfuric acid and 48 parts of acetic acid.

EXAMPLE 12

(a) 2-Acetaminonaphthalene-8-sulfonic acid

A mixture, prepared at about 15° C., of 1,025 parts of acetic anhydride and 1,500 parts of anhydrous sulfuric acid was initially introduced into the glass flask used in Example 1a. 1,117 parts of dry 2-aminonaphthalene-8-sulfonic acid were introduced, with stirring, over 1 hour at a temperature gradually rising from about 20 to about 45° C. In order to complete the acetylation, the mixture was heated to about 80° C. and further stirred at this temperature. The reaction mixture was then stirred into 2,500 parts of water at about 35° C., whereupon 2-acetaminonaphthalene-8-sulfonic acid crystallized out. The crystallization was completed by further stirring at about 15° C. After filtering off with suction, 1,800 parts of an approximately 70% pure product were obtained. This was stirred into a mixture of 1,750 parts of 31% strength hydrochloric acid and 300 parts of ice. The pale grey suspension obtained was filtered with suction at about 5° C. and washed with 580 parts of 31% strength hydrochloric acid.

1,670 parts of a 75% pure 2-acetaminonaphthalene-8-sulfonic acid hydrate which was free of sulfuric acid and contained hydrochloric acid were obtained. The product was dried in a drying oven in a stream of nitrogen under about 200 mbar at a temperature slowly rising from about 25° to about 120° C.

1,260 parts of 2-acetaminonaphthalene-8-sulfonic acid were obtained as a 97% pure powder, which corresponded to a yield of 95% of theory relative to 2-aminonaphthalene-8-sulfonic acid.

In addition, the following were obtained:

3,800 parts of an approximately 30% strength filtrate sulfuric acid which was free of salt and hydrochloric acid and could be regenerated and contained 780 parts of acetic acid, 2,250 parts of an approximately 22% strength filtrate hydrochloric acid containing 185 parts of sulfuric acid.

(b) 2-Acetaminonaphthalene-8-sulfonyl chloride.

466 parts of chlorosulfonic acid were initially introduced into the glass flask used in Example 1b and, with stirring, 265 parts of the 2-acetaminonaphthalene-8-sulfonic acid obtained according to Example 12 a were introduced over 2 hours at a temperature slowly rising from about 25° to about 50° C. After evolution of gas had ceased, 238 parts of thionyl chloride were allowed to run in over 5 hours at about 45°–50° C. After evolution of gas had ceased (SO$_2$ and HCl; their absorption took place in the customary manner described in Example 1b), the reaction mixture was stirred into 2,000 parts of ice-water (1,000 parts each of water and ice) in which 30 parts of powdered active charcoal had been suspended. The precipitated product was filtered off with suction and washed with 1,200 parts of ice-water. The wash filtrate can serve to precipitate the next batch.

283 parts of 2-acetaminonaphthalene-8-sulfonyl chloride were obtained as a technical moist product in a yield of 95% of theory relative to 2-aminonaphthalene-8-sulfonic acid.

In addition, the following were obtained:

1,660 parts of approximately 14% strength sulfuric acid which was free of salt and could be regenerated and contained 75 parts of hydrogen chloride, 1,150 parts of wash filtrate containing 40 parts of hydrogen chloride and 110 parts of sulfuric acid, 300 parts of approximately 30% strength hydrochloric acid (from the waste gas washing) containing 10 parts of $SO_2$, 375 parts of an approximately 24% strength sodium bisulfite solution which was almost free of chloride (from the waste gas washing).

EXAMPLE 13

223 parts of dried 2-aminonaphthalene-8-sulfonic acid were introduced over 1 hour, with stirring, into a mixture, prepared at about 15° C., of 205 parts of acetic anhydride, 5 parts of dimethylformamide and 300 parts of anhydrous sulfuric acid in the glass flask used in Example 1b at a temperature gradually rising from about 20 to about 40° C. In order to complete the acetylation, the mixture was heated to about 80° C. and further stirred at this temperature for 3 hours.

After cooling down to about 50° C., the solution of 2-acetaminonaphthalene-8-sulfonic acid was diluted, without intermediate isolation, with 233 parts of chlorosulfonic acid and further stirred at about 50° C. until gas evolution was finished. 833 parts of thionyl chloride were added dropwise, with stirring, over about 8 hours at about 50° C. The mixture was then further stirred at about 50° C. for 2 hours. After evolution of gas had ceased ($SO_2$ and HCl; their absorption took place in the customary manner described in Example 1b), the reaction mixture was freed of residual gases in a stream of dry nitrogen and then stirred into 2,000 parts of ice-water (1,000 parts each of water and ice) to which 30 parts of powdered active charcoal had been added. The precipitated product was filtered off with suction and washed with 2,000 parts of ice-water.

255 parts of N-acetaminonaphthalene-8-sulfonyl chloride were obtained as a technical moist product in a yield of 90% of theory relative to 2-aminonaphthalene-8-sulfonic acid.

In addition, the following were obtained:

2,000 parts of approximately 15% strength filtrate sulfuric acid which was free of salt and could be regenerated and contained 145 parts of hydrogen chloride and about 145 parts of acetic acid, 2,260 parts of wash filtrate containing 61 parts of hydrogen chloride and 170 parts of sulfuric acid, 890 parts of an approximately 35% strength hydrochloric acid (from the waste gas washing) containing 33 parts of $SO_2$ and 5 parts of acetic acid, 5,100 parts of an approximately 11% strength sodium bisulfite solution (from the waste gas washing) which was almost free of chloride (sodium chloride content 3%) and contained 4 parts of acetic acid.

EXAMPLE 14

(a) 2-Acetaminonaphthalene-6-sulfonic acid.

A mixture, prepared at about 15° C., of 1,025 parts of acetic anhydride and 1,515 parts of 99.0% strength sulfuric acid was initially introduced into the glass flask used in Example 1a. 1,117 parts of dry 2-aminonaphthalene-6-sulfonic acid were introduced with stirring over about 2 hours at a temperature gradually rising from about 20 to about 75° C. The mixture was then further stirred at about 85° C. 3 hours after the addition of the -aminonaphthalene-6-sulfonic acid, a further 255 parts of acetic anhydride were allowed to run in. In order to complete the acetylation, the mixture was further stirred at about 85° C. for 2 hours. The reaction mixture was then stirred into 3,000 parts of water at about 35° C., whereupon -acetaminonaphthalene-6-sulfonic acid crystallized out. The crystallization was completed by further stirring at about 25° C. After filtering off with suction, 3,000 parts of an approximately 35% pure product were obtained. This was stirred into a mixture of 3,500 parts of 31% strength hydrochloric acid and 1,000 parts of ice. The pale grey suspension obtained was filtered with suction at about 25° C. and washed with 2,750 parts of 20% strength hydrochloric acid.

About 2,600 parts of a 40% pure 2-acetaminonaphthalene-6-sulfonic acid hydrate which was free of sulfuric acid and contained hydrochloric acid were obtained. The product was dried in a drying oven in a stream of nitrogen under about 200 mbar at a temperature slowly rising from about 25 to about 90° C.

1,140 parts of 2-acetaminonaphthalene-6-sulfonic acid were obtained as an approximately 95% pure powder, which corresponded to a yield of 80% of theory relative to 2-aminonaphthalene-6-sulfonic acid.

In addition, the following were obtained:

3,400 parts of an approximately 25% strength filtrate sulfuric acid which was free of salt and hydrochloric acid and could be regenerated and contained 670 parts of acetic acid, 7,300 parts of an approximately 20% strength filtrate hydrochloric acid containing 440 parts of sulfuric acid and 380 parts of acetic acid.

(b) 2-Acetaminonaphthalene-6-sulfonyl chloride.

A mixture of 583 parts of chlorosulfonic acid, 15 parts of acetic anhydride and 5 parts of dimethylformamide was initially introduced into the glass flask used in Example 1b and, with stirring, 265 parts of the 2-acetaminonaphthalene-6-sulfonic acid obtained according to Example 14 a were introduced over 1 hour at a temperature slowly rising from about 20 to about 35° C. Then 238 parts of thionyl chloride were allowed to run in over 5 hours at about 55° C. The mixture was further stirred at about 55° C. for about 2 hours. After evolution of gas had ceased ($SO_2$ and HCl; their absorption took place in the customary manner described in Example 1b), nitrogen was blown through the reaction mixture and the contents of the flask were stirred, over 1 hour, into 2,200 parts of ice-water (500 parts of water and 1,700 parts of ice) in which 30 parts of powdered active charcoal were suspended. The precipitated product was filtered off with suction and washed with 1,500 parts of ice-water. The wash filtrate can serve to precipitate the next batch.

283 parts of 2-acetaminonaphthalene-6-sulfonyl chloride were obtained as a technical moist product in a yield of 80% of theory relative to 2-aminonaphthalene-6-sulfonic acid.

In addition, the following were obtained:

2,330 parts of an approximately 15% strength waste sulfuric acid which was free of salt and could be regenerated and contained 135 parts of hydrogen chloride and small amounts of acetic acid and dimethylformamide, 1,620 parts of wash filtrate containing 40 parts of hydrogen chloride and 100 parts of sulfuric acid, 300 parts of approximately 23% strength hydrochloric acid (from the waste gas washing) containing 20 parts of $SO_2$, 700 parts of an approximately 12% strength sodium bisulfite solution (from the waste gas washing) which was almost free of chloride (sodium chloride content <1%).

EXAMPLE 15

223 parts of dried 2-aminonaphthalene-6-sulfonic acid were introduced with stirring over 2 hours into a mixture, prepared at about 15° C., of 205 parts of acetic anhydride, 5 parts of dimethylformamide and 300 parts of anhydrous sulfuric acid in the glass flask used in Example 1b at a temperature slowly rising from about 20 to about 70°–85° C. In order to complete the acetylation, the mixture was further stirred at about 85° C. for 3 hours. Then a further 51 parts of acetic anhydride were added at about 50° C. and the further stirring at about 85° C. was continued for 2 hours.

After cooling down to about 50° C., the solution of 2-acetaminonaphthalene-6-sulfonic acid obtained was diluted, without intermediate isolation, with 233 parts of chlorosulfonic acid and further stirred at about 50° C. until gas evolution had finished. 833 parts of thionyl chloride were added dropwise, with stirring, over about 8 hours at about 50° C. The mixture was then further stirred at about 50° C. for 2 hours. After evolution of gas had deceased ($SO_2$ and HCl: their absorption took place in the conventional manner described in Example 1b, the reaction mixture was freed of residual gases in a stream of dry nitrogen and then stirred into 2,000 parts of ice-water (1,000 parts each of water and ice) to which 30 parts of powdered active charcoal had been added. The precipitated product was filtered off with suction and washed with 2,000 parts of ice-water.

251 parts of 2-acetaminonaphthalene-6-sulfonyl chloride were obtained as a technical moist product in a yield of 89% of theory relative to 2-aminonaphthalene-6-sulfonic acid.

In addition, the following were obtained:

2,370 parts of an approximately 15% strength filtrate sulfuric acid which was free of salt and could be regenerated and contained 117 parts of hydrogen chloride and 92 parts of acetic acid, 2,110 parts of wash filtrate containing 31 parts of hydrogen chloride and 83 parts of sulfuric acid, 887 parts of an approximately 35% strength hydrochloric acid (from the waste gas washing) containing 36 parts of $SO_2$ and 81 parts of acetic acid, 5,260 parts of an approximately 11% strength sodium bisulfite solution (from the waste gas washing) which was almost free of chloride (sodium chloride content <3%) and contained 41 parts of acetic acid.

EXAMPLE 16 (Comparison Example)

(a) 173 parts of metanilic acid (as a product moist with water) in 300 parts of water in the glass flask used in Example 1a were neutralized to give the sodium salt by the addition of the stoichiometric amount of sodium hydroxide solution. 141 parts of acetic anhydride were then allowed to run in at about 80° C. In order to complete the acetylation, the mixture was further stirred at about 80° C., the pH decreasing from about 7 to about 2. Then water and acetic acid (72 parts) were distilled out. After drying in a drying oven at 120° C. under about 200 mbar, 237 parts of sodium N-acetylmetanilate were obtained as a 97% pure product.

(b) 525 parts of chlorosulfonic acid were initially introduced into the glass flask used in Example 1b and, with stirring, 237 parts of the sodium N-acetylmetanilate obtained according to Example 16a were introduced over about 1 hour at a temperature slowly rising from about 25° to about 55° C. 238 parts of thionyl chloride were then allowed to run in, with stirring, over 5 hours at about 55° C. After evolution of gas had ceased ($SO_2$ and HCl; their absorption took place in the customary manner described in Example 1b), the reaction mixture was stirred into 1,700 parts of ice-water (1,200 parts of water and 500 parts of ice) in which 30 parts of powdered active charcoal had been suspended. The precipitated product was filtered off with suction and washed with 1,100 parts of ice-water. The wash filtrate can serve to precipitate the next batch.

210 parts of N-acetylmetanilyl chloride were obtained as a technical moist product in a yield of 90% of theory relative to metanilic acid.

In addition, the following were obtained:

2,100 parts of an approximately 20% strength waste sulfuric acid which contained salt (120 parts of $NaHSO_4$), the regeneration of which is subject to considerable interference due to the salt content, and which also contained 190 parts of hydrogen chloride and 17 parts of metanilic acid.

1,000 parts of wash filtrate containing 36 parts of hydrogen chloride and 40 parts of sulfuric acid, 300 parts of an approximately 27% strength hydrochloric acid (from the waste gas washing) containing 20 parts of $SO_2$, 400 parts of approximately 18% strength acetic acid (from Example 16a), 250 parts of an approximately 27% strength sodium bisulfite solution.

EXAMPLE 17 (Comparison Example)

The procedure was as in Example 16a with the difference that the addition of the stoichiometric amount of sodium hydroxide solution necessary for the neutralization of the metanilic acid was omitted. The metanilic acid was not acetylated.

We claim:

1. A process for the preparation of N-acetylaminophenyl-or naphthyl-sulfonic acids by acetylation of amino-phenyl- or naphthyl-sulfonic acids with acetic anhydride or acetyl chloride, which comprises carrying out the acetylation in sulfuric acid as the solvent.

2. The process as claimed in claim 1, wherein the acetylation is carried out in the presence of a minor amount of water or dimethylformamide or N-methylpyrrolidone or mixtures thereof.

3. The process as claimed in claim 1, wherein the acetylation is set up on the presence of an amount, up to 2% by weight, of water or in the presence of an amount, up to 3% by weight, of dimethylformamide or N-methylpyrrolidone, in each case relative to the sulfuric acid.

4. The process as claimed in claim 3, wherein said amounts are up to 1% by weight of water and up to 2.5% by weight of dimethylformamide or N-methylpyrrolidone.

5. The process as claimed in claim 1, wherein 2 to 3 mols of sulfuric acid per mole of aminophenyl- or naphthyl-sulfonic acid are initially introduced together with the acetylating agent.

* * * * *